United States Patent [19]
Kroll et al.

[11] Patent Number: 5,735,876
[45] Date of Patent: Apr. 7, 1998

[54] ELECTRICAL CARDIAC OUTPUT FORCING METHOD AND APPARATUS FOR AN ATRIAL DEFIBRILLATOR

[75] Inventors: Kai Kroll; Mark W. Kroll, both of Minnetonka, Minn.

[73] Assignee: Galvani Ltd., Minneapolis, Minn.

[21] Appl. No.: 548,014

[22] Filed: Oct. 25, 1995

Related U.S. Application Data

[63] Continuation of Ser. No. 754,712, Dec. 6, 1996, which is a continuation of Ser. No. 543,001, Oct. 13, 1995, abandoned, which is a continuation-in-part of Ser. No. 251,349, May 31, 1994, abandoned.

[51] Int. Cl.$^6$ ............................................ A61N 1/39
[52] U.S. Cl. ............................................................ 607/5
[58] Field of Search ...................................... 607/4, 5, 7

[56] References Cited

U.S. PATENT DOCUMENTS

| | | |
|---|---|---|
| 3,638,656 | 2/1972 | Grandjean et al. |
| 3,952,750 | 4/1976 | Mirowski et al. |
| 4,222,386 | 9/1980 | Smolnikov et al. |
| 4,349,030 | 9/1982 | Belgard et al. |
| 4,572,191 | 2/1986 | Mirowski et al. |
| 4,945,909 | 8/1990 | Fearnot et al. |
| 4,996,984 | 3/1991 | Sweeney et al. |
| 5,018,522 | 5/1991 | Mehra et al. |
| 5,042,497 | 8/1991 | Shapland et al. |
| 5,207,219 | 5/1993 | Adams et al. |
| 5,265,600 | 11/1993 | Adams et al. |
| 5,282,837 | 2/1994 | Adams et al. |
| 5,330,509 | 7/1994 | Kroll et al. |
| 5,350,402 | 9/1994 | Infinger et al. |

FOREIGN PATENT DOCUMENTS

| | | |
|---|---|---|
| 540266 | 5/1993 | European Pat. Off. |
| 9306886 | 4/1993 | WIPO |
| 9319809 | 10/1993 | WIPO |

OTHER PUBLICATIONS

Kirchhof, et al. * "Regional Entrainment of Atrial Fibrillation Studied by High Resolution Mapping in Open–Chest Dogs." Circulation 1993; 88: 736–749.

Ken Knight, et al. * "Regional Capture of Fibrillating Right Ventricular Myocardium: Evidence of an Excitable Gap in VF Using High Resolution Cardiac Mapping." J Am Coll Card 1994; 283A.

Schuder, et al. * "Transthoracic Ventricular Defibrillation in Dogs With Unidirectional Rectangular Double Pulses." Cardiovasc Res. 1970; 4: 497–501.

Kuelberg et al. * "Ventricular Defibrillation with Double Square Pulses." Med & Biol Eng., 1968; 6: 167–169.

Kugelberg, et al. * "Ventricular Defibrillation: A New Aspect." Acta Chirurgica Scandinavia 1967: 372.

Resnekov* "Ventricular Defibrillation by Monophare Trapezoidal shaped Double–pulses of Low Electrical Energy." Cardiovasc Res. 1968; 2: 261–264.

Geddes, et al. * "Ventricular Defibrillation with Single and Twin Pulses of Half–Sinusoidal Current." J Applied Physiology, 1973; 34: 8–11.

*Primary Examiner*—William E. Kamm
*Attorney, Agent, or Firm*—Patterson & Keough PA

[57] ABSTRACT

An implantable device for temporarily maintaining cardiac output through the use of electrical forcing fields in the event of an atrial defibrillation shock causing ventricular fibrillation. The device includes an atrial defibrillator. In the event that an atrial defibrillation shock causes a ventricular fibrillation the apparatus and method then delivers a continuous train of modest voltage pulses to force partial cardiac contractions to maintain life and consciousness until the patient can receive external defibrillation.

21 Claims, 15 Drawing Sheets

ELECTRICAL CARDIAC OUTPUT FORCING METHOD AND APPARATUS FOR AN ATRIAL DEFIBRILLATOR

This application is a continuation-in-part of Ser. No. 08/251,349 filed on 31 May, 1994 entitled, "Method for Apparatus for Temporarily Electrically Forcing Cardiac Output in a Tachyarrhythmia Patient" which application is now abandoned and was contined under FWC Serial No. 08/543,001 filed Oct. 13, 1995 which application was also abandoned in favor of FWC Serial No. 08/754,712 filed on Dec. 6, 1996 which is currently pending.

FIELD OF THE INVENTION

This invention generally relates to cardiac arrhythmia treatment method and control apparatus. Specifically, the present invention pertains to a backup for the treatment of atrial fibrillation by utilizing electrical cardiac output forcing method and apparatus. More specifically, the present invention pertains to an electrical method and apparatus for stimulating the cardiac cells of a patient to induce partial contraction of the heart to force cardiac output during ventricular fibrillation induced accidentally by atrial fibrillation therapy.

BACKGROUND OF THE INVENTION

Atrial fibrillation is a common occurrence in cardiac patients. Although atrial fibrillation is not acutely life threatening it is a major cause of hospitalization. It causes a lack of blood output from the atria and usually leads to blood clots in the atria. The blood dots break loose and may lodge in either the lungs or the brain resulting in serious health problems, strokes or possibly death to the patient.

Various types of drugs have been tried to treat atrial fibrillation. While some patients are helped by these drug therapies, the majority of patients are not successfully and safely treated and require a different type of treatment. One of the most significant shortcomings of these drugs is the side effects they may have on the patients. Specifically, in some patients administration of these drugs leads to a ventricular fibrillation which may be immediately fatal.

The atria are much smaller than the ventricles. Accordingly, the energy required to defibrillate the atria is much lower than that for the ventricles. Traditional prior art discloses structures in which automatic defibrillators deal with atrial defibrillation systems, see for example U.S. Pat. No. 4,572,191. Further, recently issued U.S. Pat. No. 5,265,600 covers some aspects of an implantable atrial defibrillator.

A critical element in the use of implantable atrial defibrillators is that the atrial defibrillation shock may lead to ventricular fibrillation. This is because a moderate level shock during the T-wave of the ventricle will typically lead to fibrillation. To overcome this problem, a recently issued patent, U.S. Pat. No. 5,350,402, a method in which the R-wave in the ventricle and carefully synchronize the shock so that no shock is delivered during the T-wave. Further, the risk of fibrillating the heart with an atrial defibrillation shock can also be minimized by avoiding the delivery of shocks after a certain combination of ventricular intervals as disclosed in U.S. Pat. No. 5,207,219 and U.S. Pat. No. 5,282,837.

In spite of the advances made by the prior art, atrial defibrillation shock therapy may cause ventricular fibrillation and therefore a therapy for an otherwise non-fatal condition might be fatal to the patient. One possible solution is to incorporate a ventricular defibrillator with an atrial defibrillator. However, the energy required for ventricular defibrillation is significantly higher than is required for atrial defibrillation. Therefore, the capacitors and batteries need to be large and the device would need to be the same size as a conventional implantable ventricular defibrillator.

Thus, while prior art methods and devices have performed adequately, there is an acute need for a reliable means to induce atrial defibrillation without endangering the life of the patient. Accordingly, as will be set forth below, the present invention overcomes these and other related limitations of the prior art.

SUMMARY OF THE INVENTION

The present invention provides an electrical apparatus and method to stimulate cardiac cells thereby causing a partial contraction of the heart to force cardiac output during ventricular fibrillation. Specifically, the present invention utilizes electrical forcing fields, applied to the ventricles, tailored to yield ventricular output. One of the unique aspects of the invention is the focus to maintain some ventricular output which is distinguished from a defibrillation shock which is designed to restore normal rhythm.

In the preferred embodiment, a forcing field is generated by applying approximately 30–200 volts across the ventricles at a rate of approximately 100–180 beats per minute (BPM). These electrical fields are advantageously applied after detection of a ventricular fibrillation and maintained for up to several hours. Thus, a cardiac output which is a fraction of the normal maximum capacity is generated. Realizing that the heart has a four or five times reserve capacity, the present invention strategically induces sufficient cardiac output which is a fraction of normal pumping activity to maintain life and consciousness. Further, the present invention implements various waveforms to optimize the electrical efficiency or patient comfort.

The present invention is also related to co-pending applications entitled "Temporary Electrical Cardiac Forcer For Implantation in High-risk Cardiac patients" filed on Oct. 25, 1995, Ser. No. 08/548,013 and "Method and Apparatus For Electrically Forcing Cardiac Output as a Backup For Anti-tachycardia Pacing" filed on Oct. 26, 1995, Ser. No. 08/548,234 by the same inventors. These applications are incorporated herein by reference.

The method and apparatus of the invention includes an electronic system advantageously integrated with a lead system adapted to deliver defibrillation shocks to the atrium. It also includes a lead system and electronics for delivering electrical cardiac output forcing pulses to the ventricle in the event that the atrial defibrillation shock leads to ventricular fibrillation. In the event that the atrial defibrillation shock leads to ventricular fibrillation, the electrical cardiac output forcing (ECOF) system will force cardiac output for a period of up to several hours thus giving the patient enough time to get to a hospital. Further, this feature of the present invention enables rescue crews enough time to arrive and perform an external defibrillation.

Accordingly, the present invention provides a method and apparatus to monitor and treat atrial fibrillation within a safe and reliable margin. Specifically, this invention includes an atrial defibrillation treatment system with a safety feature incorporated to treat resultant ventricular fibrillation which may arise due to the electric shock administered during the atrial defibrillation treatment and/or the progressive deterioration of the patient's cardiac condition.

DESCRIPTION OF THE PREFERRED EMBODIMENT

The invention will now be described more fully hereinafter with reference to the accompanied drawings in which preferred embodiments of the invention are shown. This invention may, however, be embodied in many different forms, and should not be construed as limited to the embodiments set forth hereto. Rather, applicants provide these embodiments so that this disclosure will be thorough and complete and will convey the scope of the invention to those skilled in the art.

Figure 1:
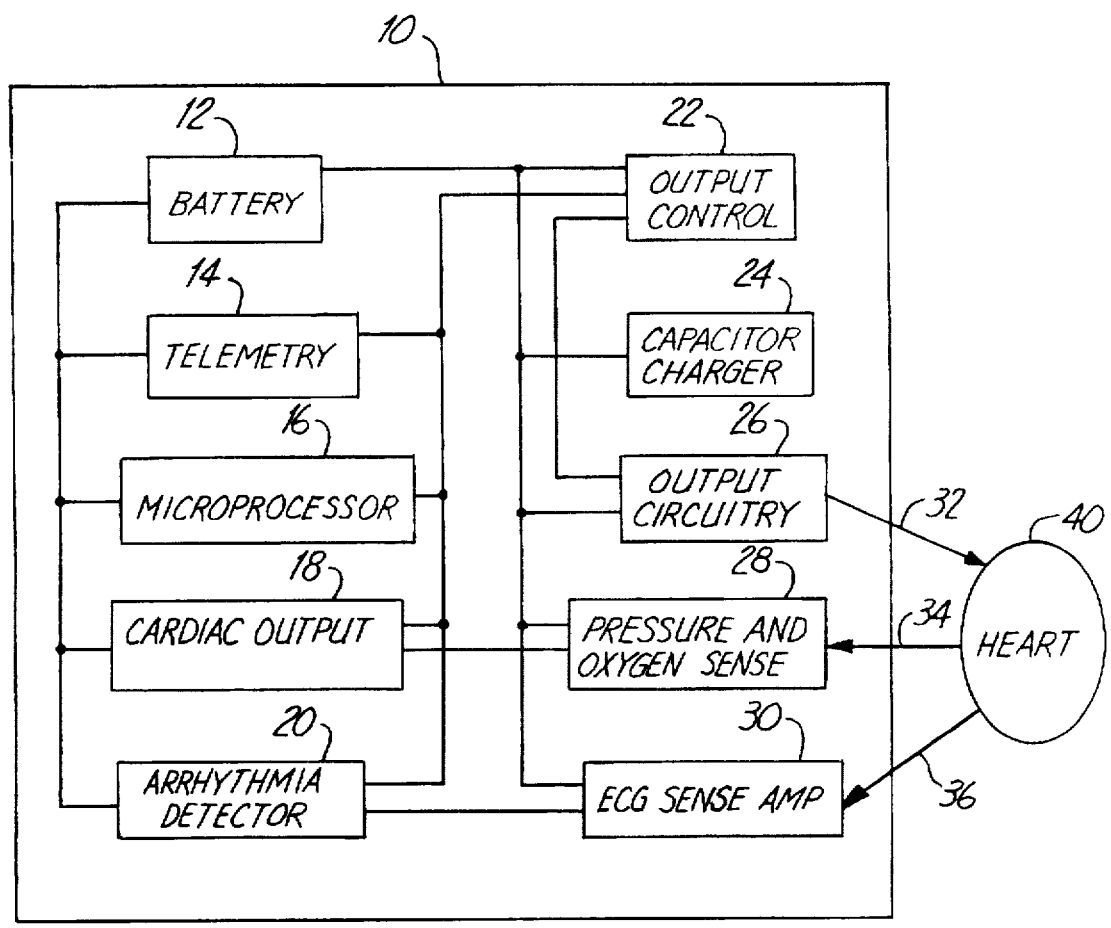
FIG. 1 is a block diagram illustrating a system constructed in accordance with the principles of the present invention.

FIG. 1 is a block diagram illustrating a system 10 constructed in accordance with the principles of the present invention. The device circuitry is connected to the heart 40 via a series of leads; output lead 32, pressure sense lead 34, and ECG sense lead 36. The electronic circuit includes a conventional ECG amplifier 30 for amplifying cardiac signals. The amplified cardiac signals are analyzed by a conventional arrhythmia detector 20 which determines if an arrhythmia is present. The arrhythmia detector 20 may be one of several types well known to those skilled in the art and is preferably able to distinguish between different types of arrhythmias. For example; atrial or ventricular fibrillation, tachycardia or asystole. The circuit also contains an optional pressure sensing section 28 which amplifies and conditions a signal from an optional pressure sensor from within the heart or artery. The output of the pressure sense circuit 28 is fed to a cardiac output detection circuit 18 which analyzes the data and determines an estimate of the cardiac output. Data from the arrhythmia detector circuit 20 and the cardiac output detection circuit 18 is fed to the microprocessor 16. The microprocessor 16 determines if Electrical Cardiac Output Forcing (ECOF) is appropriate. If forcing is indicated, the microprocessor 16 prompts the output control 22 to charge a capacitor within the output circuit 26 via the capacitor charger 24. The output control 22 directs the output circuitry 26 to deliver the pulses to the heart 40 via the output leads 32. The microprocessor 16 may communicate with external sources via a telemetry circuit 14 within the device 10. The power for the device 10 is supplied by an internal battery 12.

Figure 2:
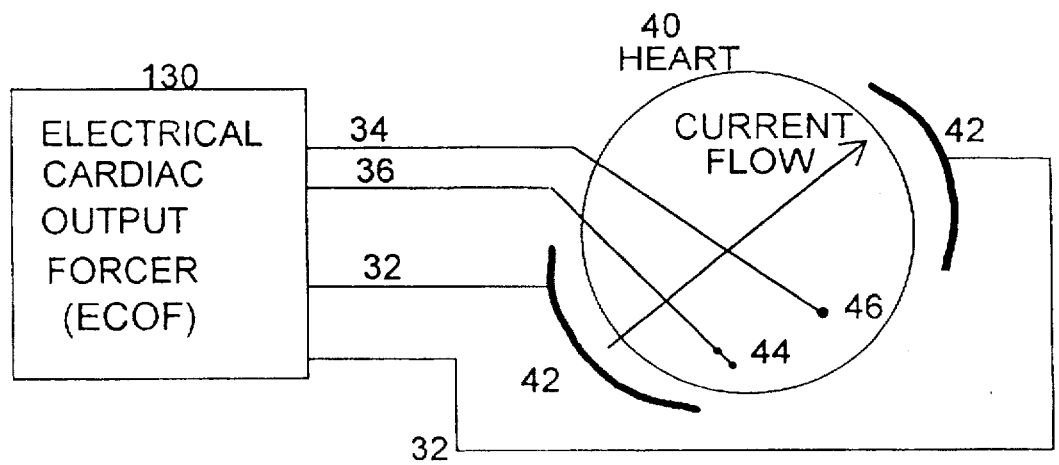
FIG. 2 shows a connection of an implantable embodiment of the device to the heart in an epicardial patch configuration.

FIG. 2 is a diagram showing the connection of an implantable embodiment of the backup portion of the device 130 to the heart 40 in an epicardial patch configuration. In this thoracotomy configuration, current passes through an output lead pair 32 to electrode patches 42 which direct the current through the heart 40. There is an optional pressure sense lead 34 which passes the signal from an optional pressure transducer 46 which lies in the heart 40. The ECG is monitored by sense electrodes 44 and passed to the device 130 by a lead 36. The area of the electrodes 42 is a least 0.5cm2. The size of the electrode is greater than that of a pacing lead and no more than that of a defibrillation electrode or between approximately 0.5cm2 and 20 cm2 each.

Figure 3:
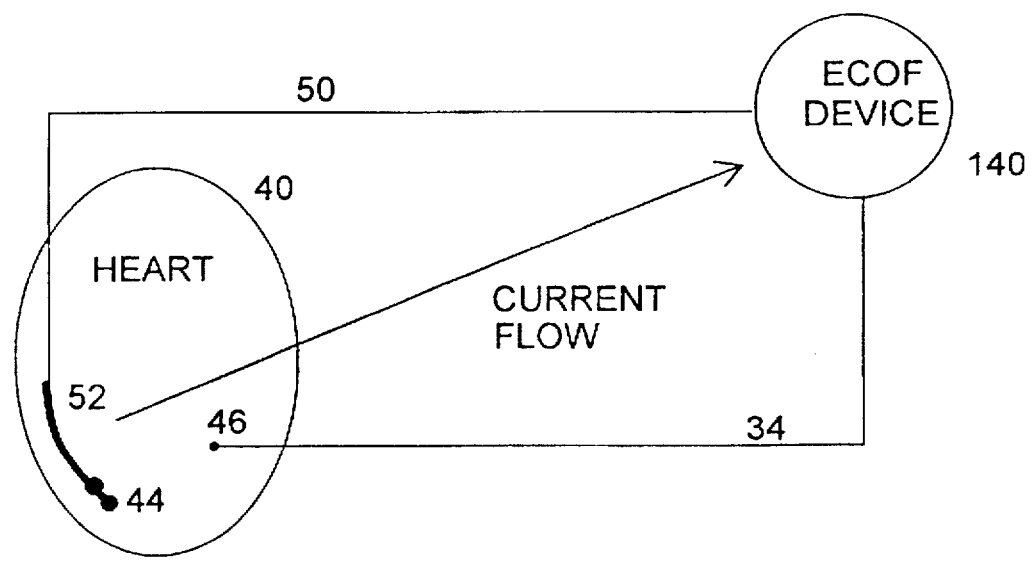
FIG. 3 shows the connection of an implantable embodiment of the device to the heart using an endocardial lead system and the device housing as an electrode.

FIG. 3 shows a non-thoractomy system embodiment of the backup portion of the invention. In this system, the current passes from a coil electrode 52 in the heart 40 to the housing of the device 140. An endocardial lead 50 combines the ECG sensing lead and the pulse output lead. The ECG is monitored by sense electrodes 44 in the heart 40 and passes through the endocardial lead 50. There is an optional pressure transducer 46 in the heart 40 which passes a signal to the device 140 via optional lead 34.

Figure 4:
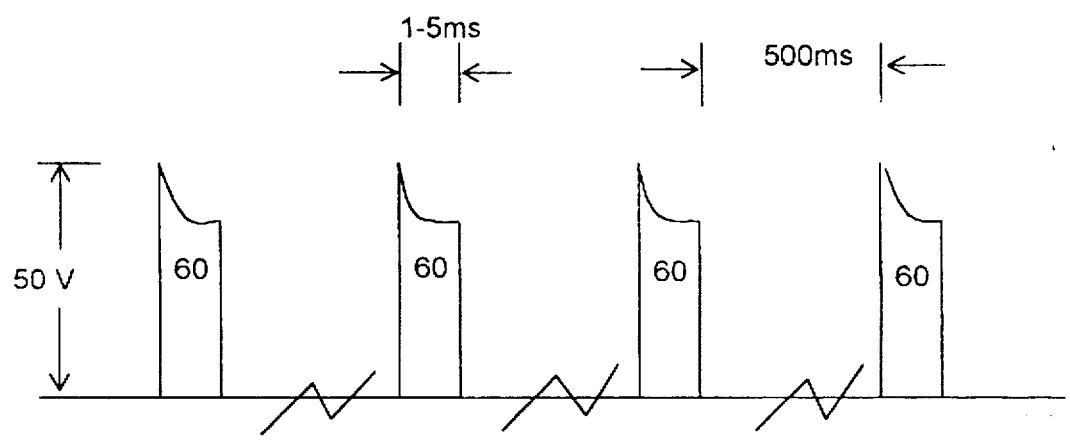
FIG. 4 is a diagram showing a representative pulsatile electrical signal.

A series of forcing pulses 60 are shown in FIG. 4. The pulses are approximately 50 V in amplitude with a spacing of approximately 500 ms. The 50 V and the 500 ms pulse spacing are chosen as illustrative for an implantable embodiment. The forcing pulse interval is chosen to maximize cardiac output within the limits of the device circuitry and the response of the heart muscle. An interval of 500 ms corresponds to a heart rate of 120 beats per minute. This will produce a greater output than a typical resting rate of 60 beats per minute. However, a rate of 240 beats per minute would produce a lower output due to mechanical limitations of the heart. Thus a practical range is 60 to 200 beats per minute is appropriate. The pulses could also be timed to coincide with the natural pumping of the atria, thus improving overall cardiac output.

The higher the voltage, the higher the forcing fields, and therefore a greater number of heart cells contracting producing greater cardiac output. However, the higher voltage produces greater patient discomfort and extraneous muscle twitching.

Implantable batteries are also limited to a certain power output and energy storage. If an output pulse is 50 V and the electrode impedance is 50Ω the power during the pulse is $P=V^2/R=50V*50V/50 \Omega=50$ W. If the pulse has a duration of 2 ms then the energy per pulse is 0.1 J. If two pulses are delivered every second, the charger must be capable of delivering 0.2 J per second which is 200 mW. This is well within the limits of an implantable battery. An implantable battery can typically deliver 5 W of power. However, 200 V pulses at 3 per second would require 4.8 W which is near the limit of the battery and charging circuitry. A typical implantable battery energy capacity is 10,000 J. Delivering forcing pulses at a rate of 4.8 W would deplete the battery in only 35 minutes. (10,000J/4.8 W=2083 seconds). Thirty five minutes may not be enough time to transport the patient to a hospital. Therefore 200 V represents the highest practical voltage for continuous operation in an implantable embodiment, although voltages of up to 350 V could be used for short periods and adjusted down when hemodynamic output is verified. A practical lower limit is about 10 V. During normal sinus rhythm, 10 V delivered through the patches would pace. However, during fibrillation the 10 V could not pace and only cells very near the electrodes would be captured. This would be insufficient for forcing cardiac output.

Assuming a compromise voltage of 30 V and an electrode impedance of 100Ω, the forcing current would be 300 milliamperes although the system would provide more if necessary.

These calculations also suggest other differences between an implantable ECOF and an ICD. With a battery storing 10,000 J and an ECOF pulse having 0.1 , this ECOF would be capable of delivering 100,000 pulses. An ICD can only deliver 200–400 shocks of about 30 J. The ECOF is also very different from an implantable pacemaker which typically delivers 150,000,000 pacing pulses (5 years at 60 BPM) each of about 0.00005 J.

Figure 5:
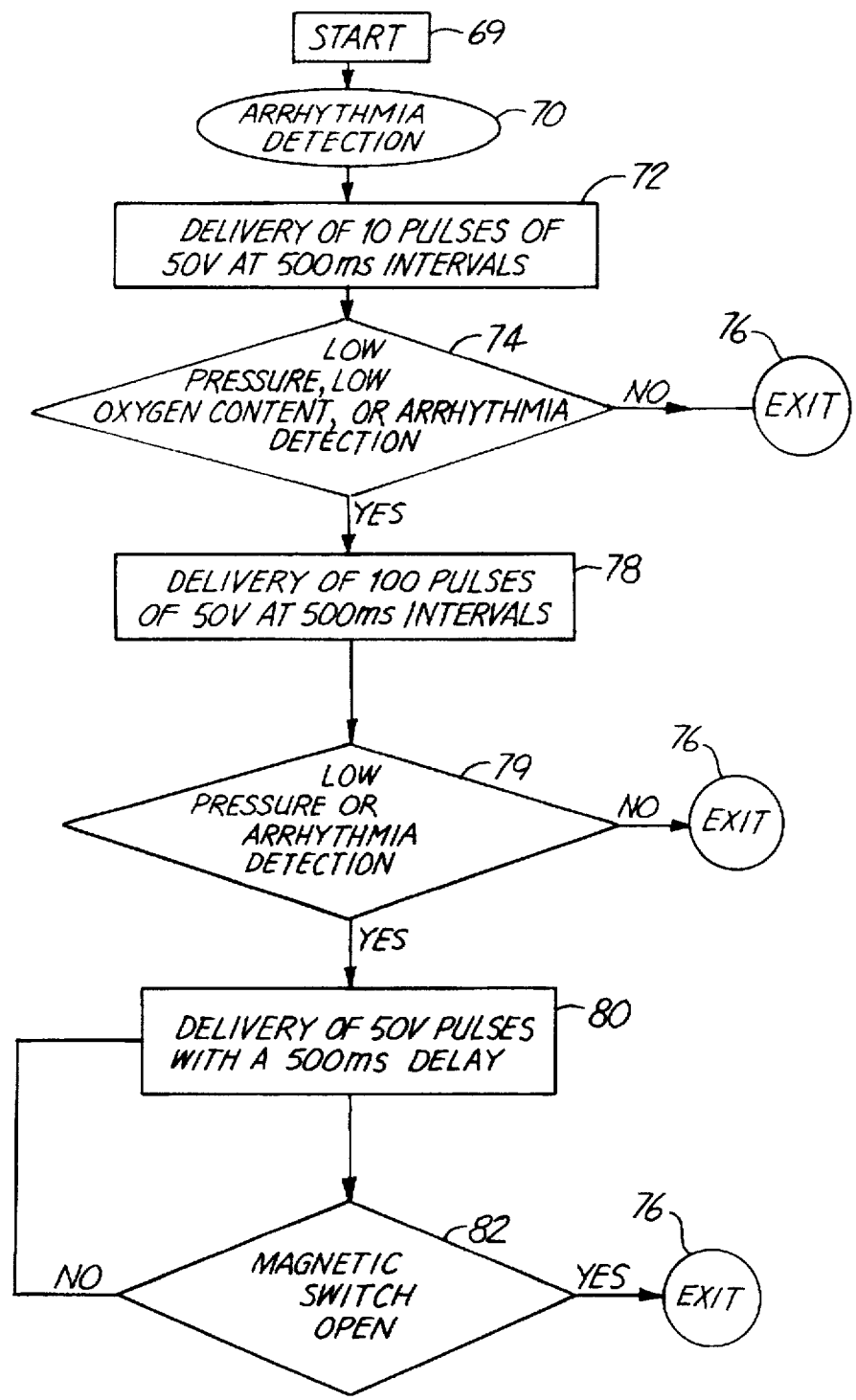
FIG. 5 is a flowchart illustrating the ECOF backup method of the invention.

FIG. 5 is a flowchart illustrating the method of the ECOF backup portion of the invention, which is provided for purposes of illustration only. One skilled in the art will recognize from the discussion that alternative embodiments may be employed without departing from the principles of the invention. The flow diagram shown in FIG. 5 represents a method of automatically treating a heart which is in ventricular fibrillation (due to acceleration from an atrial defibrillation shock) and thereby pumping inefficiently or not at all. After the start 69 a diagnoses of the presence of a ventricular arrhythmia is made 70. A series of cardiac output forcing electric pulses 72 is automatically delivered. It should be understood that the therapy 72 may be delivered for any output compromising cardiac arrhythmia. After delivery of 10 forcing pulses (at a rate of 60–200 BPM) in the first block 72, the status of the heart is determined 74. If an arrhythmia is still present and there exists low pressure within the heart, more forcing pulses are delivered 78. If the heart is pumping at a safe level, the therapy ceases and exits 76. After the therapy 78 has been delivered, the pressure and ECG is again monitored 74. If the therapy 78 is successful, it ceases and exits 76. If the therapy 78 is unsuccessful in producing a safe level of pumping efficiency, the method proceeds to a continuos cardiac assist mode 80. The therapy may only be stopped by an external command, for example, a telemetry signal or a magnet which is applied to the chest activating a magnetic reed switch 82 which terminates the therapy and exits 76. To minimize patient discomfort and maximize battery life, the forcing voltage could be adjusted down when sufficient pressure signals or adequate flow measured by other means were detected, for example, the pressure sense transducer could be replaced by an oxygen detector or a doppler flow measuring device. The pulse rate could also be adjusted to maximize output.

Figure 6:
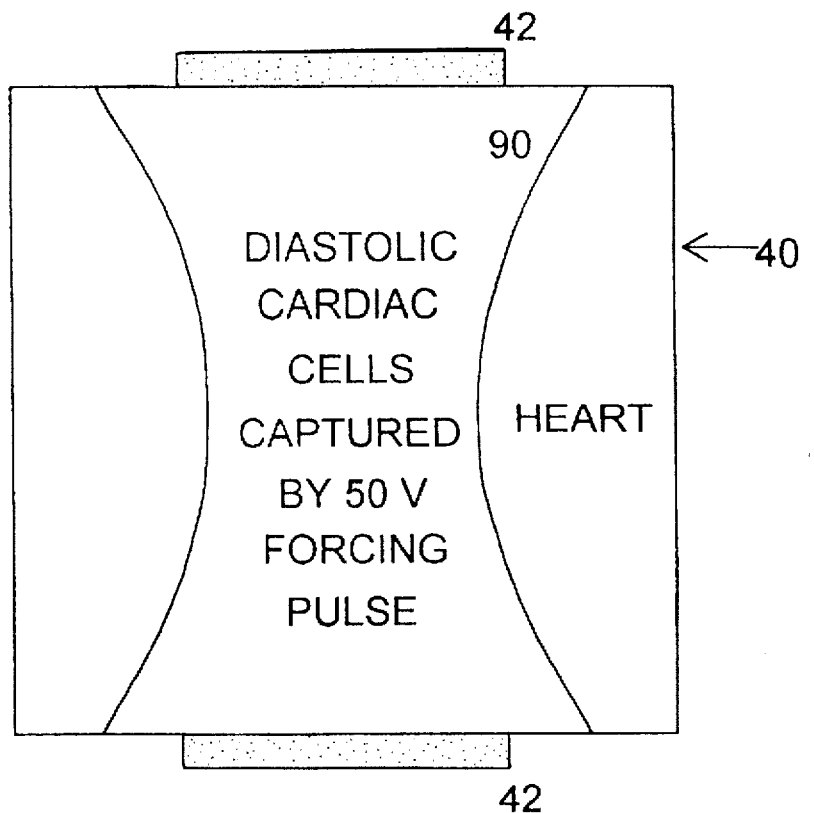
FIG. 6 is a diagram showing the expected effect of a 50 V pulse on the heart during diastole.

FIG. 6 is a diagram showing the effect of a 50 V forcing pulse on the heart 40 during electrical diastole (cells at rest). The current is passed through the heart 40 by the electrodes 42. Approximately 60% of cardiac cells 90 would be captured by a 50 V pulse if the cells were in diastole. The captured cells 90 mostly lie in the direct path between the electrodes 42 and near the electrodes 42 where the field strengths are highest. Of course, over a time period of about 100 ms these directly captured cells then propagate an activation wavefront to stimulate the rest of the heart. This so called far-field pacing is irrelevant here as the hearts, of interest, are in fibrillation and not in diastole.

Figure 7:
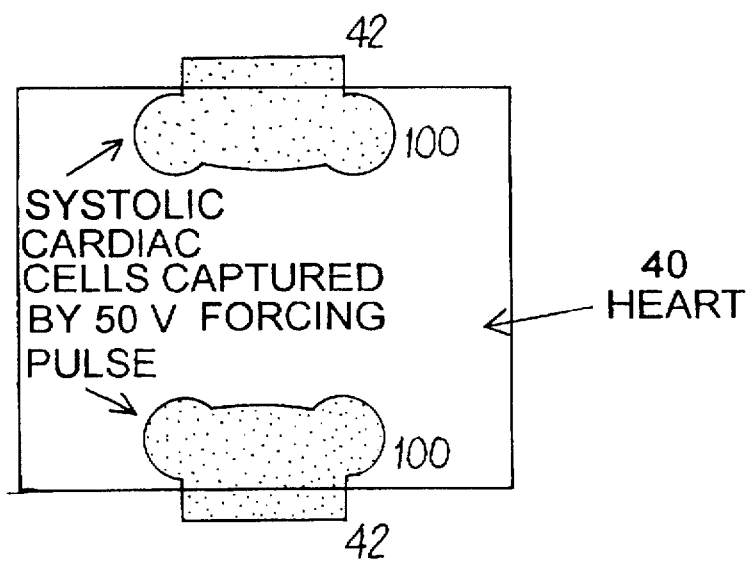
FIG. 7 is a diagram showing the expected effect of a 50 V pulse on the heart during systole.

FIG. 7 is a diagram showing the effect of a 50 V forcing pulse on the heart during electrical systole (cells already stimulated). The current is passed through the heart 40 by the electrodes 42. Approximately 20% of cardiac cells 100 would be captured by a 50 V pulse if the cells were in systole. The captured cells 100 are nearest each electrode 42 where the field strengths are highest. Capture in systolic cells means that their activation potential is extended. This capture requires significantly higher fields (10 V/cm than those required for diastolic cell capture (1 V/cm).

Figure 8:
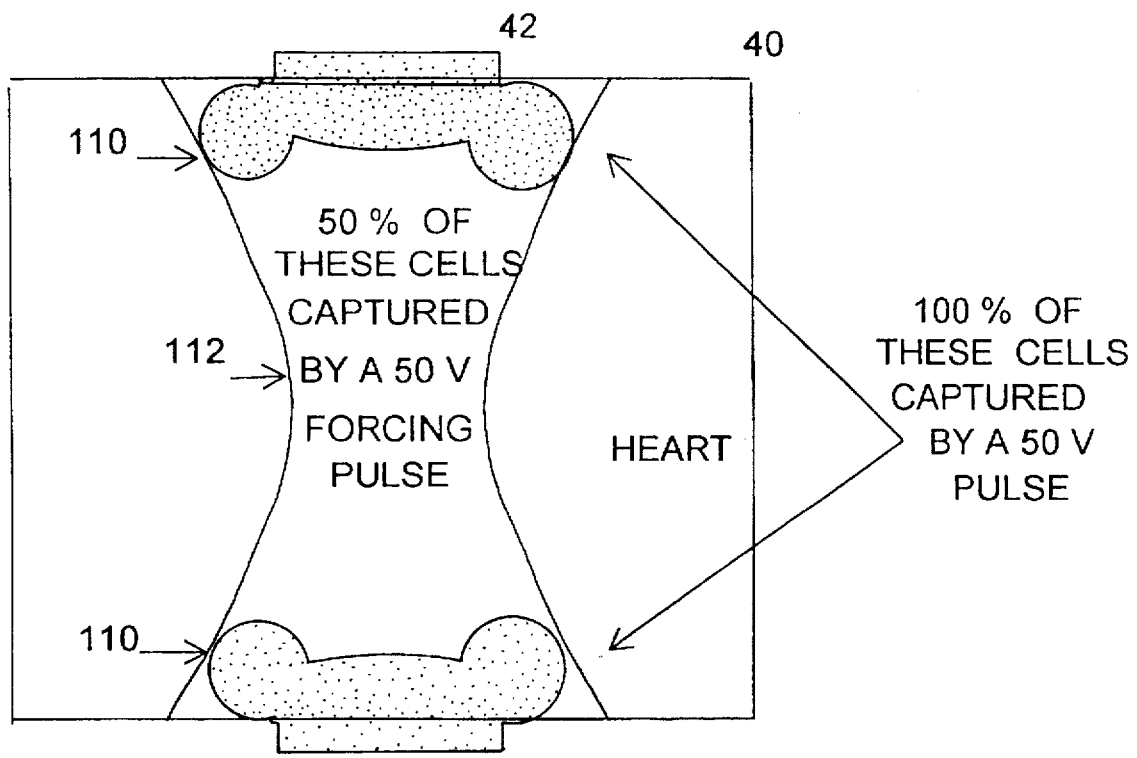
FIG. 8 is a diagram showing the expected effect of a 50 V pulse on the heart during fibrillation.

FIG. 8 is a diagram showing the effect of a 50 V forcing pulse on the heart during fibrillation. During fibrillation there are always cells in systote and diastole simultaneously. But, the vast majority are in systole. The diagram assumes 50% of the cells are in diastole which applies only after several capturing pulses. The current is passed through the heart 40 by the electrodes 42. 100% of the cells 110 nearest the electrodes 42 would be captured due to the high field strength. As shown in FIG. 7, even systolic cells are captured by high field strengths. 50% of the cells 112 in the direct path between the electrodes 42 would be captured if it is assumed that 50% of all cells are in diastole. If roughly 60% of cardiac cells are captured by a 50 V pulse when the cells are in diastole, and 20% are captured when in systole, and if 50% are in systole and 50% in diastole, 40% would be captured during fibrillation. This calculation is shown in the following table. The last two columns give the mechanical action resulting and the contribution to forcing a cardiac output.

Considering the cardiac cells that are originally in diastole, (rows A&B in the table below), the A row represents the diastolic cells that are not captured by the forcing pulse. If 50% of the heart's cells are in diastole and 40% of those are not captured that is 20% of the total cells. These cells will, however, shortly contract on their own (from previous wavefronts or new ones) providing a positive gain in mechanical action and therefore cardiac output. The B row corresponds to the diastolic cells that are captured. If 60% of the diastolic cells (50% of total) contract due to the forcing field this is 30% of the total heart cells. These cells provide the biggest gain in mechanical action and cardiac output. Next considering the activity of the systolic cells (rows C&D), if 50% of the heart's cells are in systole and 80% of those are not captured (row C), that is 40% of the heart's cells. These cells soon relax and negate a portion of the cardiac output. The systolic cells that are captured (row D) are 10% of the heart's cells (20% of 50%). These cells will hold their contraction and be neutral to cardiac output. The net result is a gain in contraction which forces cardiac output.

| Original Status of the Cells | Percentage of the Cardiac Cells | Status of the Cardiac Cells | Percentage of the Original Status | Percentage of the Total Cells | Mechanical Action | Forcing Cardiac Output Effect |
|---|---|---|---|---|---|---|
| (A) Diastolic | 50% | Diastolic non-captured | 40% of 50% | 20% | will start to contract on own | positive (+) |
| (B) Diastolic | | Diastolic captured | 60% of 50% | 30% | contract | positive (++) |
| (C) Systolic | 50% | Systolic non-captured | 80% of 50% | 40% | will start to relax on own | negative (−) |
| (D) Systolic | | Systolic captured | 20% of 50% | 10% | hold | neutral (0) |
| TOTAL | 100% | | 100% | 100% | some contraction | positive (+) |

The net result over a 200 ms mechanical response is given in the next table. The major contribution is in row (B) from the captured diastolic cells contracting.

| Row | Status of the Cardiac Cells | Change in Output | Description of Activity |
|---|---|---|---|
| A | Diastolic non-captured | +5% | Positive. Some cells will begin to contract on their own. |
| B | Diastolic captured | +30% | Positive. Cells contract due to forcing field |
| C | Systolic non-captured | −5% | Negative. Some cells will begin to relax on their own. |
| D | Systolic captured | 0% | Neutral. Cells hold contraction due to forcing field. |
| Net Gain | | +30% | A net gain in cardiac output due to forcing fields. |

The 30% net pumping action should be sufficient to maintain survival and consciousness, because the heart has a 4-5 times reserve capacity.

Figure 9:
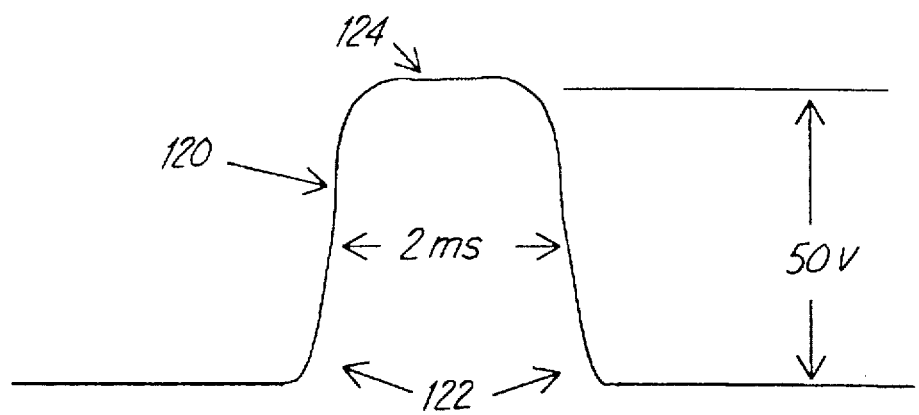
FIG. 9 shows a waveform useful for the electrical cardiac output forcing method and apparatus.

FIG. 9 depicts an example of a waveform designed to minimize the twitching of the chest muscles which can be very uncomfortable to the patient. A low harmonic pulse waveform 120 which has a very gradual "foot" 122 and a gradual peak 124. Such a pulse has less high frequency energy components and thus is less likely to stimulate the skeletal muscle.

Figure 10:
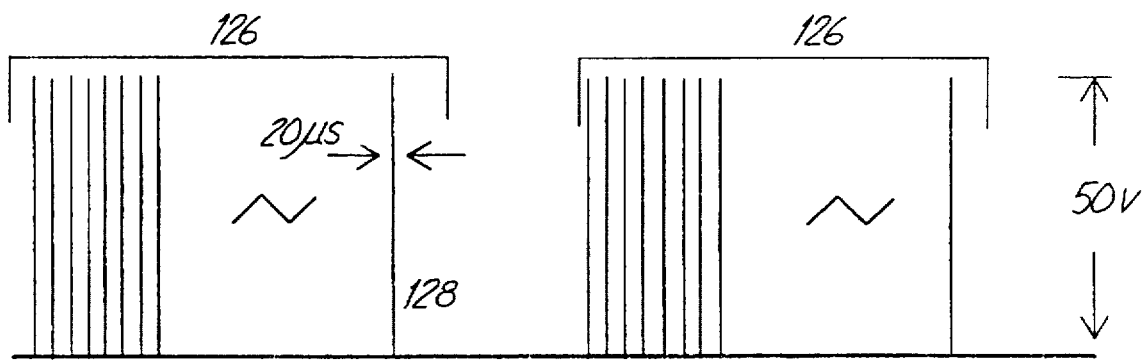
FIG. 10 shows another such waveform.

FIG. 10 shows a technique of going to the opposite extreme. Here, each compound forcing pulse 126 is actually composed of 50 very short spikes 128 each of which is 2μs spacing in width with a 20 μs spacing. The heart will tend to average out these thin pulses and "see" a 2 ms wide forcing pulse. The skeletal muscle, however, is not efficiently stimulated by these extremely narrow pulses. The skeletal muscle will not average out this signal either. This approach could help minimize skeletal muscle twitching and discomfort.

Figure 11:
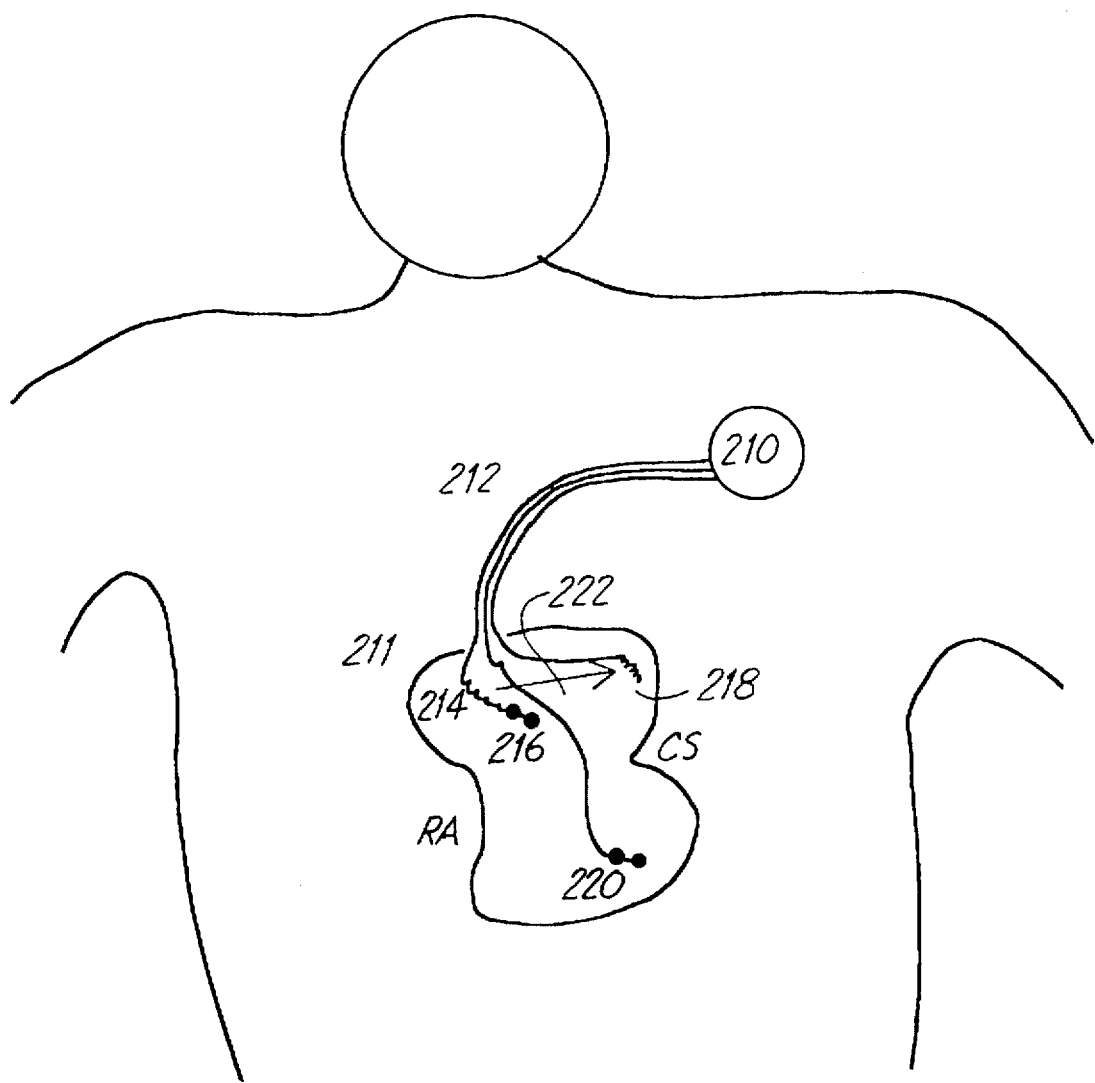
FIG. 11 shows a basic atrial implantable defibrillator in the human body.

FIG. 11 shows the basic atrial defibrillator implanted in the human body. Here the electronic system is enclosed in housing 210 with a lead set 212 connecting to the heart 211. Note that the housing is preferably implanted in the left ventricle region of the patient.

Figure 12:
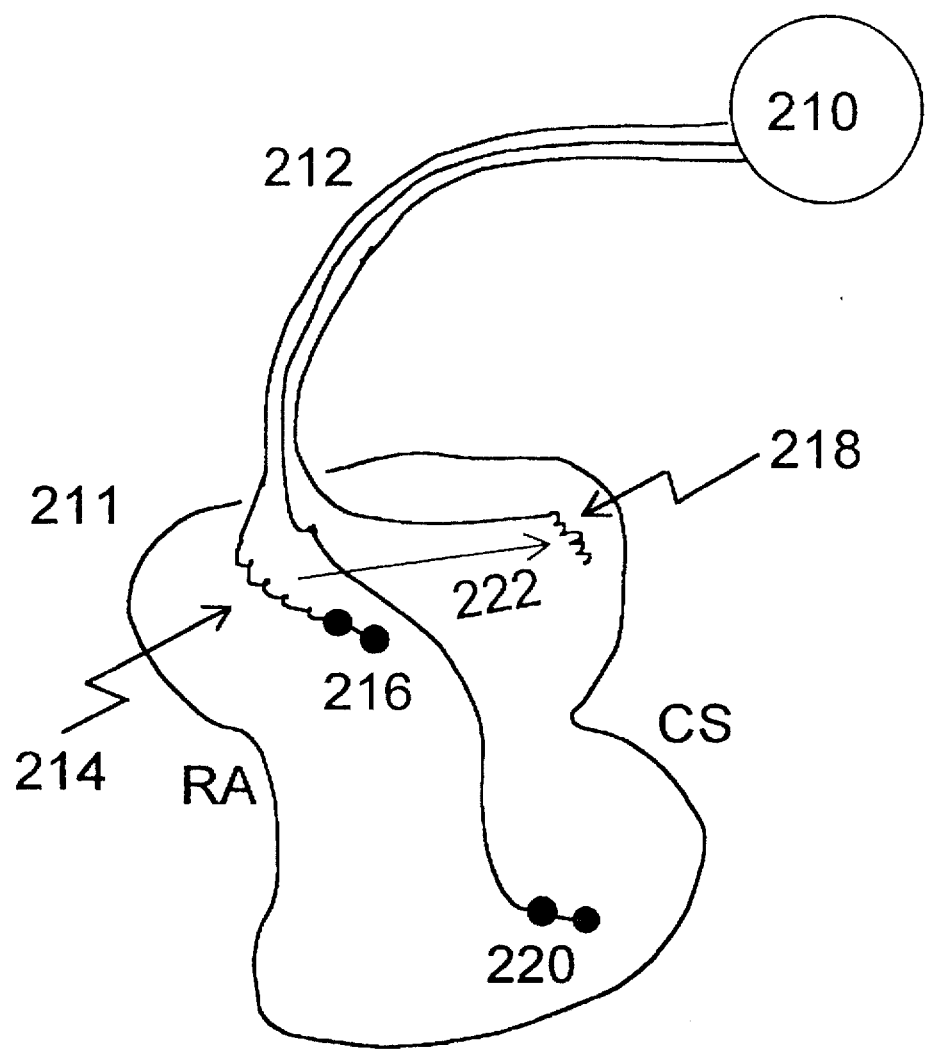
FIG. 12 shows the basic lead system for such an atrial implantable defibrillator.

FIG. 12 shows a detailed view of the leads used for the implantable atrial defibrillator. An atrial lead coil 214 is used for shock delivery and sensing pair 216 is used for sensing the rhythm in the right atrium. The lead coil 214 is typically placed in the right atrial appendage for optimum shock current delivery. Another coil 218 is located in the coronary sinus. Thus these coils are as far apart as they can be practically spaced inside atria. The atrial defibrillation shock is delivered between the coils 214 and 218 producing the electrical current path 222.

A bipolar sensing pair 220 is located in the right ventricle. This sensing pair is used for many purposes, but primarily for synchronization to minimize the risk of delivering the atrial defibrillation shock in the middle of the ventricular T-wave.

Figure 13:
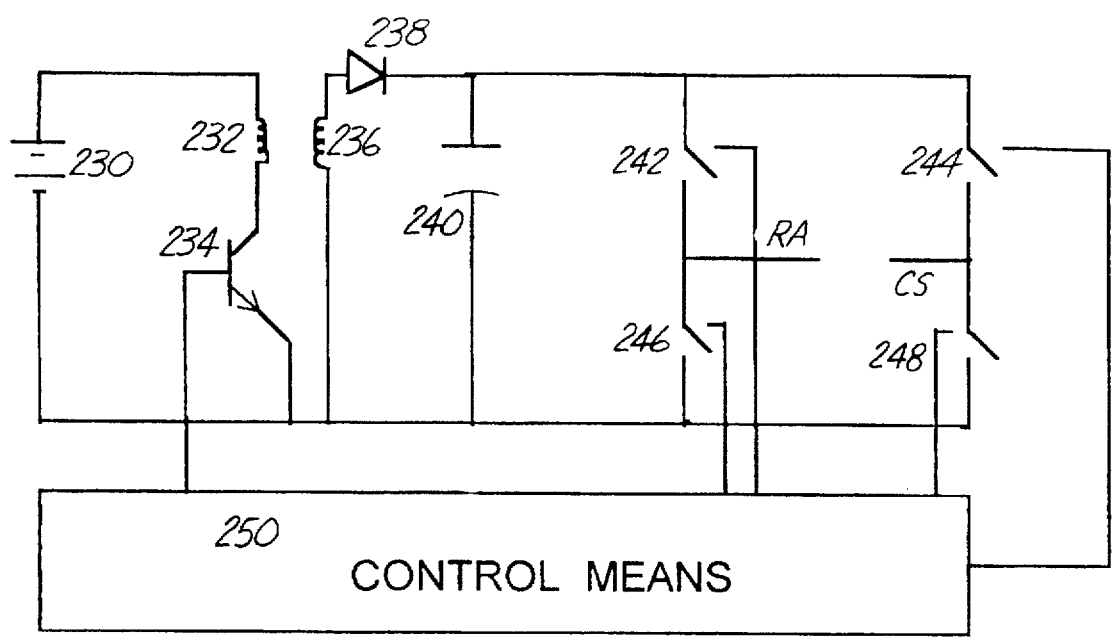
FIG. 13 shows the basic schematic for an implantable atrial defibrillator.

FIG. 13 gives a schematic of the conventional atrial implantable defibrillator. Battery 230 is used to deliver current through flyback transformer primary 232 on an interrupted basis which is caused by transistor switch 234 being controlled by the control means 250. The electrical output from a transformer is delivered by secondary winding 236 through diode 238 and stored in high energy capacitor 240. The energy in the high voltage capacitor 240 is delivered to the heart electrodes of the right atrium and coronary sinus through an "H bridge" circuit. For delivery of the positive portion of the biphasic wave switches 242 and 248 are turned on thus passing current from the RA (right atrial) lead to the CS (coronary sinus) lead. After a brief period of time those switches are opened then, switches 244 and 246 are turned on so that the current is passed into a reverse direction creating a biphasic pulse.

Figure 14:
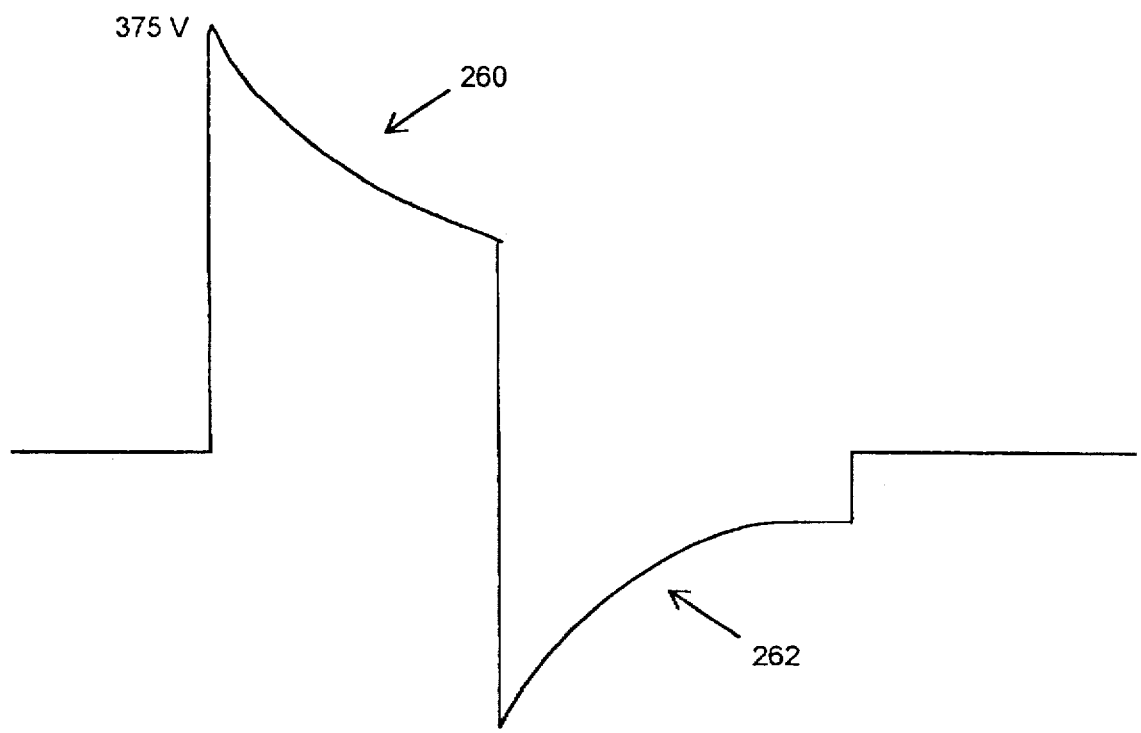
FIG. 14 shows the biphasic waveform which is used for atrial defibrillation.

FIG. 14 shows the biphasic waveform generated by the circuitry in FIG. 12. The first (or positive) phase 260 begins at a 375 volt maximum. After this phase is completed a negative phase 262 begins.

Figure 15:
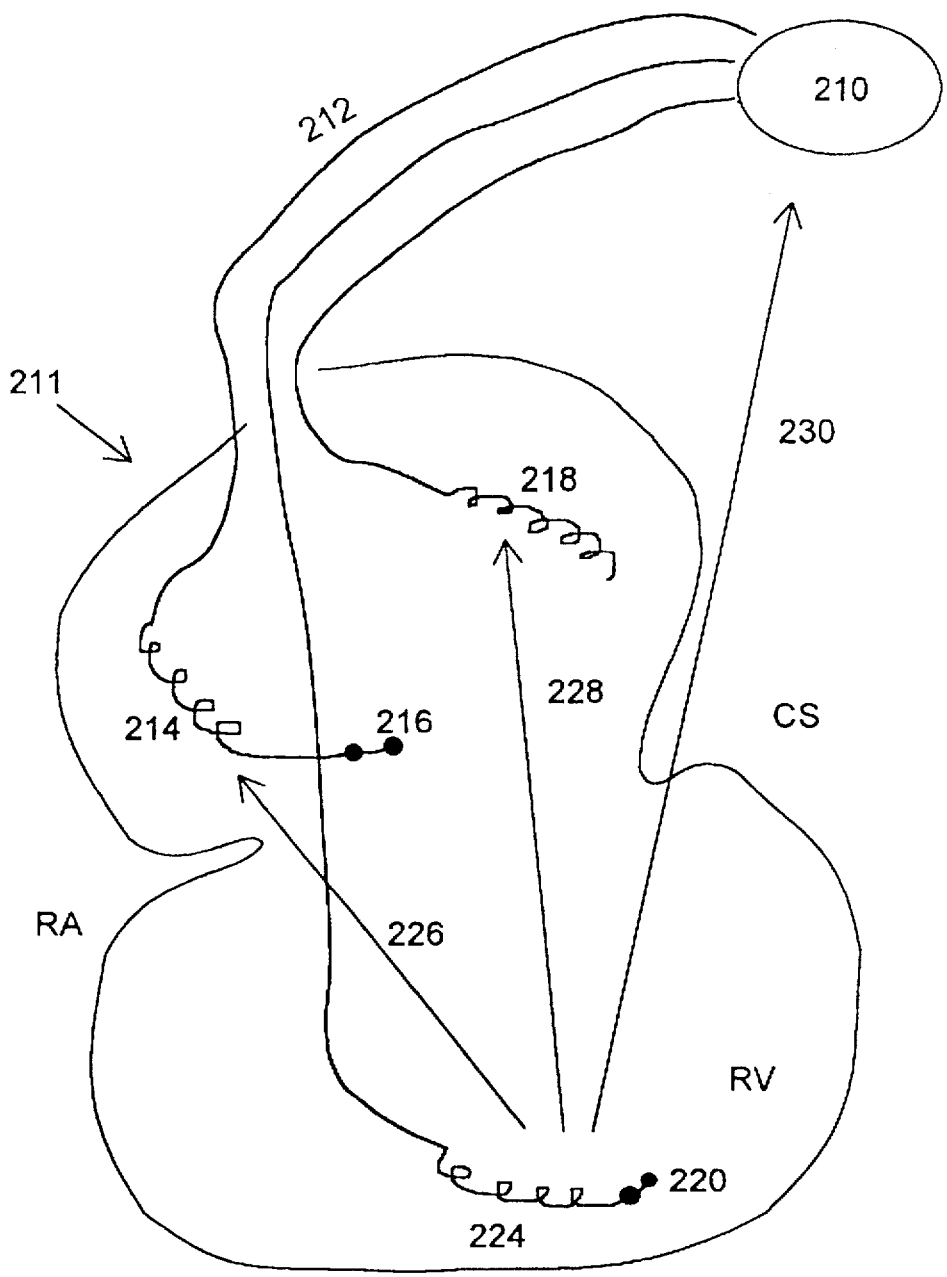
FIG. 15 shows the basic lead system for the device of this invention.

FIG. 15 shows the lead system in one embodiment for the instant invention. Two electrodes are added to the conventional lead system for an implantable atrial defibrillator. These are a right ventricular coil 224 and the device housing 210 which is now connected electrically to function as another electrode. Atrial defibrillation is performed as before for the implantable atrial defibrillator of the conventional design. However, in the event that the delivery of the atrial defibrillation shock led to ventricular defibrillation then the electrical cardiac output forcing operation is begun using the coil 224 in the right ventricle. In the simplest configuration the right atrial coil 214, the coronary sinus coil 218, and the Can housing 210 are all connected in parallel. The right ventricle thus passes current simultaneously along current paths 226, 228, and 230.

Alternatively the upper electrodes could be cycled to provide a more varied electric field across the heart to possibly engage more of the heart cells in contributing to the partial ECOF contraction. For example, the right atrial lead 214 could be operated separately. In this embodiment the right atrial lead would receive every second ECOF pulse. The intervening ECOF pulses would be delivered to the parallel combination of the coronary sinus 228 and the Can as an electrode 210.

Figure 16:
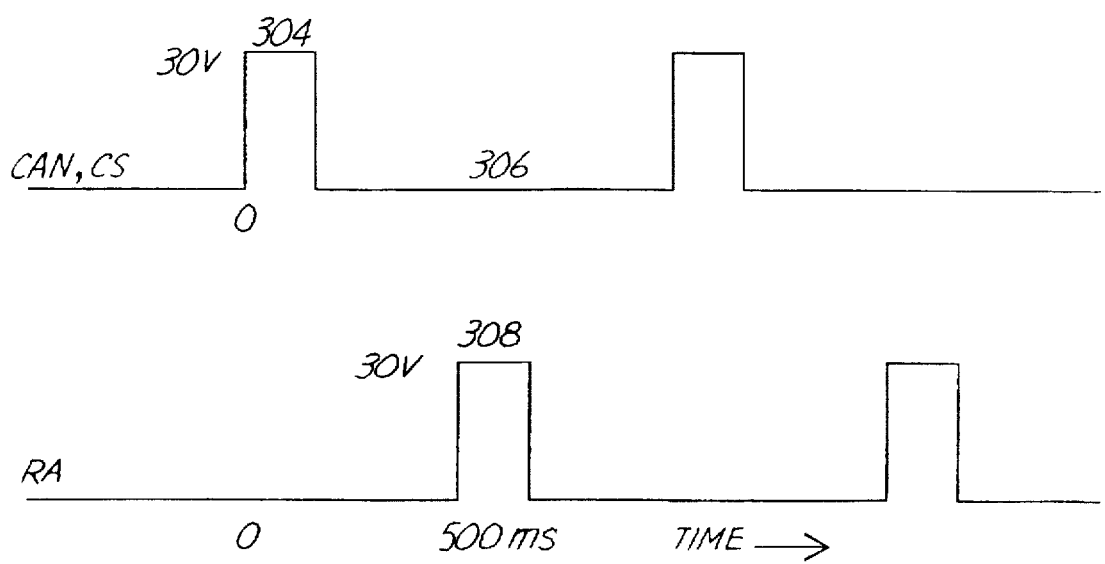
FIG. 16 shows the basic waveforms of the electrically cardiac output forcing approach used for the backup in case of ventricular fibrillation.

FIG. 16 shows the waveforms when the Can and coronary sinus leads are connected together, but the RA is separate. In this case, those two electrodes receive a 30 V pulse 304 every 1 second. In the middle of the intervening space 306 between these pulses, the right atrium receives a 30 V pulse 308.

Figure 17:
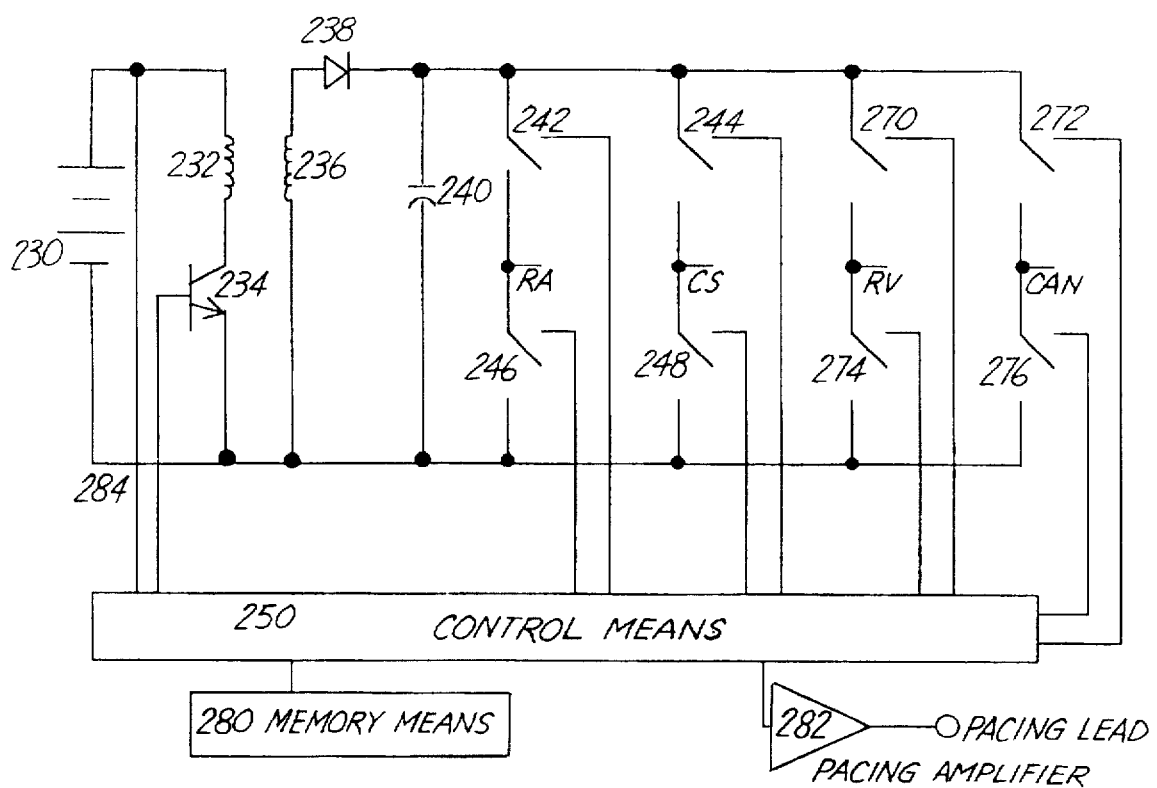
FIG. 17 shows the basic schematic of the apparatus for this invention.

FIG. 17 depicts the basic schematic of the instant invention. This is very similar to the implantable atrial defibrillator except for two significant departures. First of all there are distinct controls for the right ventricular coil and the device "Can". The right ventricular coil is controlled by switches 270 and 274 while the Can electrode is controlled by switches 272 and 276. The separate switches low for timing and pulse width variations. For example, the RA and CS switches could conduct current prior to the RV and CAN assisting in atrial output prior to ventricular ECOF. The RA and CS switches could also have a shorter pulse width so the majority of the current is transferred between the RV and CAN.

Another significant difference is that the control means allows for the use of moderate continuously generated voltages of a capacitor 240 by the continuous operation of transistor switch 234. This keeps the reverter running so a moderate voltage is maintained on capacitor 240 for a continuous delivery of the ECOF pulses. Alternatively the transistor 234 could be run at a lower duty cycle so that the voltage across capacitor 240 is minimized.

The control means 250 is connected to memory means 280 to allow the storage of programming parameters and electrograms. Also pacing amplifier 282 allows the delivery of bradycardia pacing pulses. Battery connection 284 allows the control means to monitor the battery voltage at all times thus determining its status.

Figure 18:
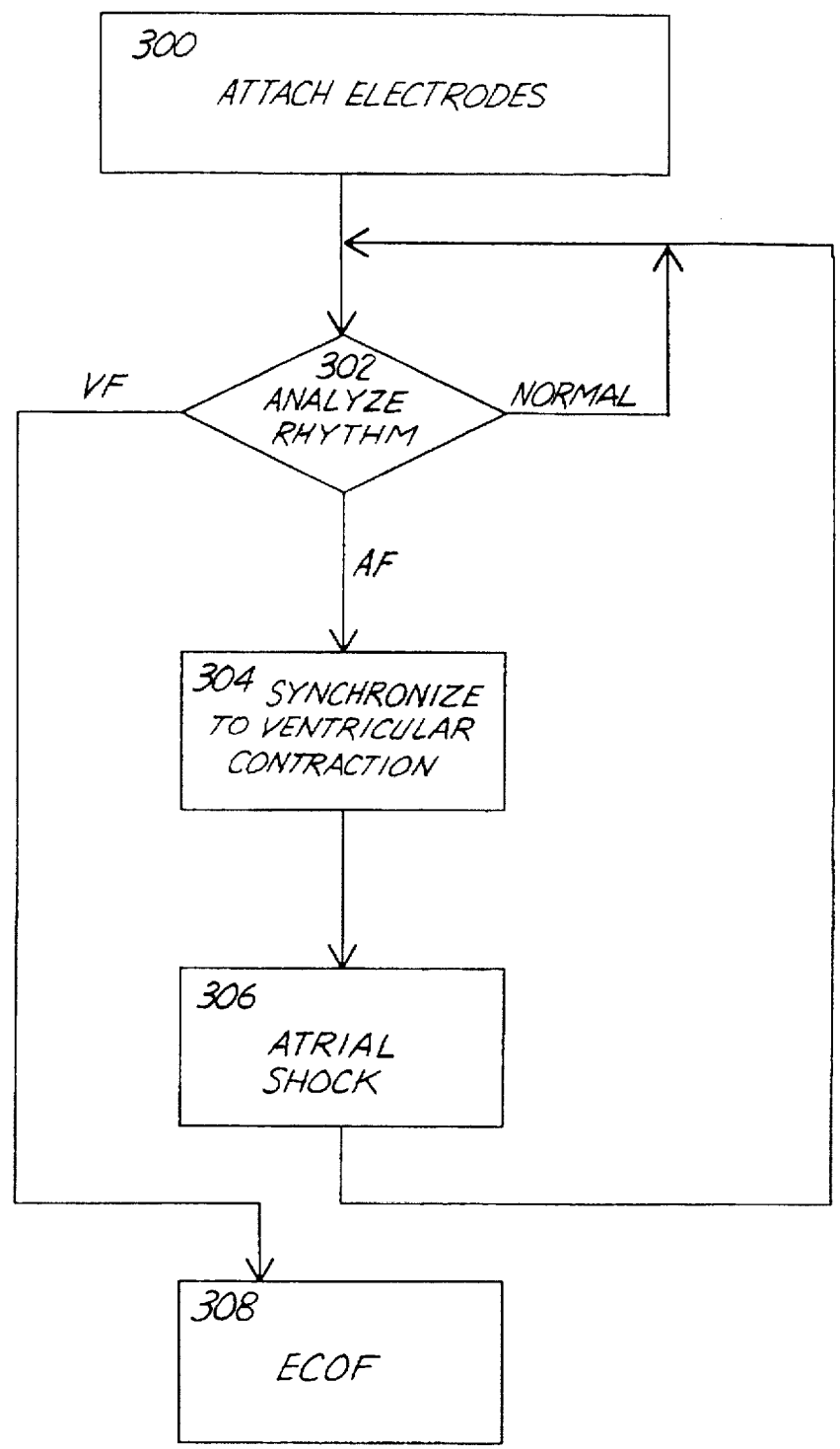
FIG. 18 shows the basic method of the invention.

FIG. 18 depicts the primary method of the invention. First electrodes are attached 300 and then the rhythm is analyzed 302. If ventricular fibrillation is detected then electrical cardiac output forcing would be performed 308. If atrial defibrillation was detected then the ventricular contraction would be synchronized to 304 and an atrial shock delivered 306. In ECOF step 308, the voltage and therapy delivery can be varied. The voltage is varied based on level of cardiac output. The pulse shape based on battery level.

It should be understood that various alternatives to the embodiments of the invention described herein may be employed in practicing the invention. It is intended that the following claims define the scope of the invention and that structures and methods within the scope of these claims and their equivalents be covered thereby.

That which is claimed is:

1. An implantable device for inducing electrical cardiac output in cooperation with an atrial defibrillation therapy system wherein the electrical cardiac output is triggered in the event of atrial defibrillation therapy causes ventricular fibrillation, the device including the atrial defibrillation therapy system comprising:

a power supply system;
   a high voltage pulse generating circuit being in electrical communication with said power supply;
   at least one electrode adapted for placement in a patient's atrium having electrical connections to said high voltage pulse generating circuit;
   control means connected to the high voltage pulse generating circuit to deliver a voltage pulse via said at least one electrode when the atrial fibrillation is detected;
   said power supply system, said high voltage, said electrode and said control means being in electrical communication and structured to form said atrial defibrillation therapy system;
   a charging circuit connected to said power supply capable of generating voltage pulses of 30–375 volts at a rate of least one pulse per second;
   a capacitor for storing energy from said charging circuit;
   at least one large electrode adapted to be placed in a patient's ventricle;
   an output circuit having electrical communication with a capacitor for delivering voltage pulses to said at least one large electrode wherein said voltage pulses are administered upon sensing ventricular fibrillation; and
   said charging circuit, said capacitor, said large electrode and said output circuit being in electrical communication and structure to form said implantable device and further having electrical communication and cooperation with said atrial defibrillation therapy system.

2. The apparatus of claim 1 wherein said large electrode includes dimensional parts which vary from a smaller section to a bigger section, the bigger section being greater than one centimeter.

3. The device of claim 1 in which said generated voltage pulses of 30–375 V include at least one gradual edge profile such that said voltage pulses rising from 30 to 375 volts require at least 100 microseconds.

4. The device of claim 1 in which each of said generated voltage pulses further includes at least six narrow pulses in parallel formation.

5. The device of claim 1 wherein said at least one electrode is same as said large electrode.

6. The device of claim 1 wherein said at least one electrode adapted to be placed in the atrium is structured to cooperate with said large electrode to provide a current path to thereby trigger the electrical cardiac output.

7. The device of claim 6 wherein the electrical cardiac output width is shorter than said voltage pulse applied to said at least one electrode adapted for placement in the atrium to direct said voltage pulse into the atrium and further said electrical cardiac output being sequenced to be deliverable prior to the voltage pulse being directed into the atrium.

8. A method of electrically controlling an atrial fibrillation in a patient wherein an atrial defibrillation therapy system results in ventricular fibrillation and an implantable device in cooperation with the atrial defibrillation therapy system supplies an electrical cardiac output upon sensing the onset of the ventricular fibrillation, comprising the device-implemented steps of:

providing a plurality of electrodes adaptable to be placed at one of proximate and inside a patient'heart;
   detecting presence of atrial fibrillation in said patient's heart;
   delivering an electrical shock to said patient's heart upon detection of an onset of said atrial fibrillation;
   monitoring for possible ventricular fibrillation; and
   delivering a series of electrical pulses to said patient's heart at a rate between 60 and 200 pulses per minute and at a voltage of between 30 and 375 volts to induce contraction in the patient's ventricle and to enable a minimum cardiac electrical output sufficient to maintain life.

9. The method of claim 8 wherein each of said series electrical pulses includes a formation structure having a gradual rise times greater than 100 microseconds such that said pulses are adaptable for use in human patients wherein said gradual rise minimizes patient discomfort and chest twitching.

10. The method of claim 8 further comprising the step of forming each of said series of electrical pulses of a discreet train of at least 10 narrow pulses to minimize patient discomfort and chest twitching.

11. The method of claim 8 further comprising the step of delivering a current above 300 milliamperes to induce said electrical cardiac output.

12. The method of claim 8 further comprising the step of storing atrial fibrillation sensing events in a microprocessor memory.

13. The method of claim 8 further comprising the step of storing ventricular fibrillation sensing events in a microprocessor memory.

14. The method of claim 8 in which one of said plurality of electrodes is adapted to be placed in the atrium of the patient's heart and further that said electrode is implemented to deliver said electrical pulses to the heart to induce contraction in the patient's heart.

15. An implantable device including an atrial defibrillation system and a ventricular fibrillation control system wherein resultant ventricular fibrillation is caused by the atrial defibrillation system during a treatment of a heart patient, the implantable device comprising:

a power supply system;

means for detecting fibrillation having electrical connection to said power supply system;

means for integrating said power supply system and said means for detecting fibrillation to be adaptable for placement in the patient's heart; and means for controlling electrical output connected to said means for detecting, said power supply system and said means for integrating to deliver a series of electrical pulses to the heart upon detection of a ventricular fibrillation wherein said series of electrical pulses include a voltage between 30 and 375 volts to force a minimum level of cardiac output sufficient to maintain life.

16. The device of claim 15 further comprising means for pacing the heart for bradycardia wherein a slow heart beat is paced back to within a normal beat per minute range.

17. The device of claim 15 in which said means for controlling electrical output includes a high energy and further includes an inverter powered by said power supply system.

18. The device of claim 15 wherein said means for controlling includes a voltage multiplier powered by said power supply system.

19. The device of claim 15 further comprising means for storing data including programmable parameters and the patient's detected internal electrical signals wherein said means for storing is implemented in a microprocessor to store and process the data.

20. The device of claim 15 further comprising means for communicating with a device external to the patient's body such that a communication and data exchange structure is implemented between said implantable device and said external device.

21. The device of claim 15 further comprising means for indicating operational status of said power supply system.

* * * * *